United States Patent [19]

Kulin et al.

[11] Patent Number: 4,500,788
[45] Date of Patent: Feb. 19, 1985

[54] DEVICE FOR PROVIDING ANTIBACTERIAL RADIATION

[75] Inventors: Ralph Kulin, Marengo; Daniel B. Granzow, Ingleside; Brant R. Danielsen, Round Lake Beach, all of Ill.

[73] Assignee: Baxter Travenol Laboratories, Inc., Deerfield, Ill.

[21] Appl. No.: 524,704

[22] Filed: Aug. 19, 1983

[51] Int. Cl.³ .................. A61L 2/10; A61M 31/00
[52] U.S. Cl. ...................... 250/455.1; 604/29; 604/244; 604/283; 604/411; 604/905
[58] Field of Search .............. 250/455.1; 604/29, 244, 604/283, 411, 905

[56] References Cited

U.S. PATENT DOCUMENTS

| | | | |
|---|---|---|---|
| 4,196,730 | 4/1980 | Wilson | 604/905 X |
| 4,412,834 | 11/1983 | Kulin et al. | 604/29 |
| 4,433,244 | 2/1984 | Hogan | 250/455.1 |
| 4,439,193 | 3/1984 | Larkin | 604/29 X |

OTHER PUBLICATIONS

Document entitled "Noncircular Gears" by Cunningham Industries, Inc.
*Nephrology Nurse*, "CAPD For the Blind", Mar./Apr., 1981, pp. 53-54.

Primary Examiner—Alfred E. Smith
Assistant Examiner—Jack I. Berman
Attorney, Agent, or Firm—Garrettson Ellis; Paul C. Flattery; John Kirby

[57] ABSTRACT

Apparatus for automatically connecting and disconnecting a pair of connectors includes first and second relatively movable means to carry the connectors and to move them back and forth between connected and disconnected positions. Rack and gear means may be used having a variable mechanical advantage at different positions to facilitate connection and disconnection of the connectors. The apparatus may also have means for providing radiation for antibacterial effect on the connectors, typically ultraviolet radiation.

22 Claims, 9 Drawing Figures

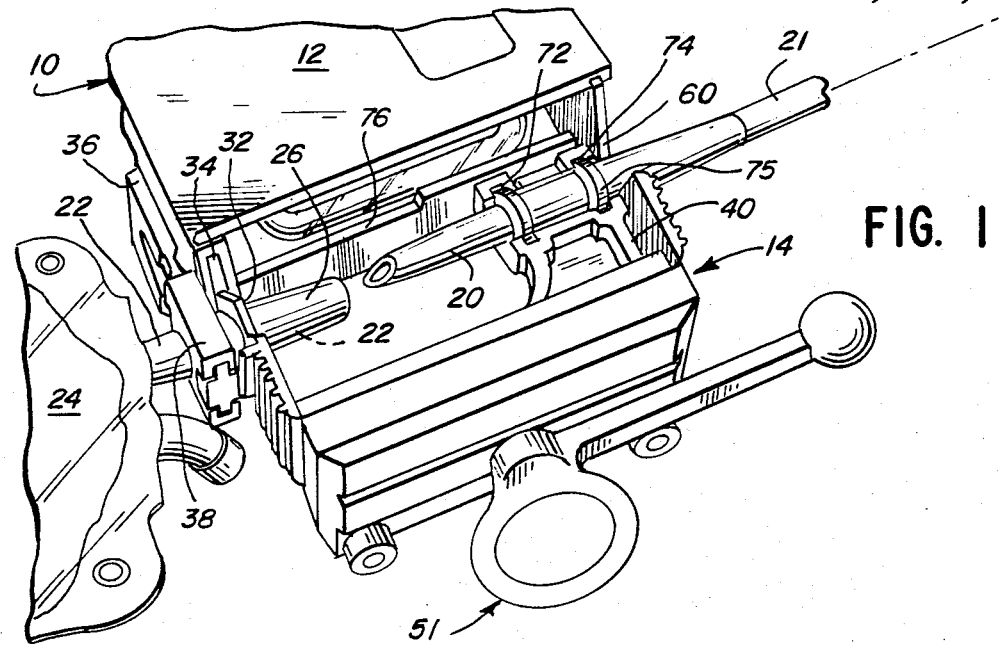
FIG. 1
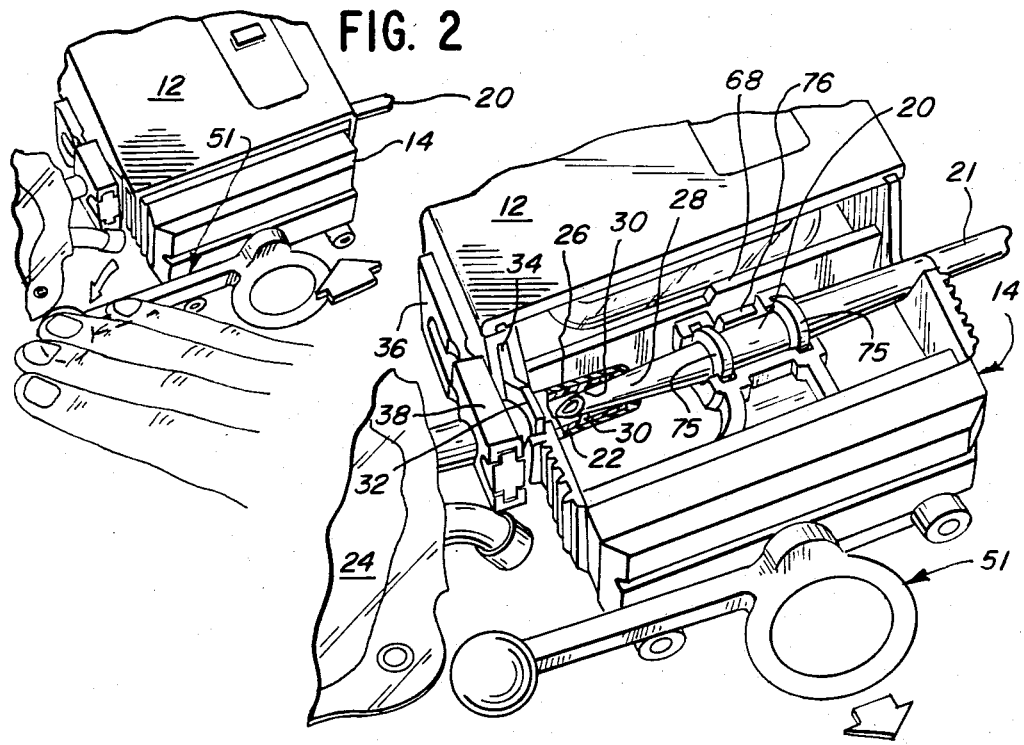
FIG. 2
FIG. 3

DEVICE FOR PROVIDING ANTIBACTERIAL RADIATION

TECHNICAL FIELD AND PRIOR ART

In various fields of medicine and elsewhere, and particularly in continuous ambulatory peritoneal dialysis (CAPD) there is a need to make and break connections between peritoneal tubing communicating with the peritoneal cavity and a source of peritoneal dialysis solution with substantially sterile procedure. At the same time it is desirable for patients undergoing CAPD or another form of peritoneal dialysis on a chronic basis to be released from close supervision by medical personnel and permitted to do the dialysis solution exchange procedures independently at their homes or places of work. However, the need for maintenance of substantially sterile procedure remains critical if peritonitis is to be avoided, particularly in the case of patients on CAPD.

In response to this, various systems for irradiation of connectors have been proposed, and one has been commercially developed, in which at least the outer connector is made of ultraviolet transparent material, and after the connectors are brought together but before seals are released to permit flow of solution through the newly formed connection, the connectors are irradiated with ultraviolet light for antibacterial effect outside and inside the connectors. See Popovich and Moncrief Pat. No. 4,475,900 entitled "PERITONEAL DIALYSIS METHOD"; Kulin et al. U.S. Pat. No. 4,412,834, entitled "ANTIMICROBIAL ULTRAVIOLET IRRADIATION OF CONNECTOR FOR CONTINUOUS AMBULATORY PERITONEAL DIALYSIS" now U.S. Pat. No. 4,412,834; and Hogan Pat. No. 4,433,244, entitled "APPARATUS FOR IRRADIATING TUBING CONNECTORS now U.S. Pat. No. 4,433,244. In all of the three pending U.S. patent applications, ultraviolet radiation is used for antibacterial effect in the newly formed connection.

Patients who are undergoing peritoneal dialysis on a chronic basis are often elderly, ill, and debilitated. The disease which requires their life maintenance by dialysis interferes with nerve conductivity which, in turn, reduces their manual dexterity. Accordingly, it becomes desirable in the case of many patients to provide them with all assistance possible in the making and breaking of connections during peritoneal dialysis and particularly CAPD operations.

In response to this, automatic systems for making and breaking connections have been provided. For example, the Steri-Track device which has been used and which is described in an article entitled "CAPD For the Blind" from the periodicial Nephrology Nurse, March/April, 1981, pp. 53-54. This device is a self-contained portable device. When doing bag exchanges, a fresh bag of dialyzate is placed into a stationary end of a holder. At this point the protective tab of the bag is removed, and a spike is taken from the discharge bag and fitted into the grooves of a sliding plate. The patient now manipulates the sliding plate toward the bag with the result that the spike will plunge into the port of the bag with alleged 98 percent probability.

Also, Munsch et al. patent application No. 416,785, filed Sept. 10, 1982, shows an improved device for automatic connection and disconnection of connectors in CAPD and the like.

In accordance with this invention, an automatic connection and disconnection system is provided, preferably in conjunction with a radiation system for exerting antibacterial effect on connectors before or after joining, in a peritoneal dialysis system or other system as may be desired. By this invention a variable mechanical advantage advancement system of the first and second means that carry the respective connectors is provided so that, preferably, even a debilitated person can exert the amount of force necessary to make and break the connection between the connectors, while at the same time the connectors can be separated by a desired substantial distance with a simple short motion of the handle.

This and other advantages and features are more fully described in the description below.

DESCRIPTION OF THE INVENTION

In accordance with this invention apparatus for automatically connecting and disconnecting a pair of connectors is provided. The apparatus includes first and second means for respectively holding the connectors, the first and second means being relatively movable between first and second positions, to cause connectors carried in the first and second means to be separated from each other in the first position, and to cause the carried connectors to be joined together in the second position. Typically, the relatively movable relationship of the first and second means is accomplished by having the first means stationary and the second means movable. However, the converse may be true and, if desired, both of the means may be movable.

Rack and gear means are provided for relatively moving the first and second means because the first and second positions. The gear of the rack and gear means defines gear teeth of increasing pitch, i.e., distance of the center point of each gear tooth from the gear's center of rotation. This increasing pitch relationship is defined about at least a portion of the periphery of the gear.

The rack of the rack and gear means defines mating teeth correspondingly spaced along its length in positions to permit relatively linear motion between the rack and gear as the gear rolls along the rack. As the result of this, the mechanical advantage of the rack and gear means varies with the position of the gear along the rack because of the varying pitch of the gear teeth. Preferably, the mechanical advantage is substantially at a maximum when the rack and gear means are at the second position.

In other words, the gear teeth which engage the teeth of the rack at the second position are of minimum pitch, i.e., their distance to the center of rotation is minimum, resulting in the highest mechanical advantage in the system. Accordingly, it becomes easier for anybody including debilitated patients to make or break a tight, frictional connection or disconnection, assisted by the increased mechanical advantage of the rack and gear means at this second position, which corresponds to the connected position of the connectors.

However, as the connectors are pulled apart, the mechanical advantage decreases as the gear moves along the rack, with teeth of increasing pitch being in contact with the rack. Accordingly, after the original, tight, frictional connection between the connectors is broken, the mechanical advantage is reduced, causing the rack to move faster as the gear rotates at a constant rate.

Thus, the simple operation of the handle to disconnect the connectors results in an initial, high mechanical advantage for breaking the connection, and then a reduced mechanical advantage to cause the connectors to thereafter move apart more rapidly, for less required motion of the handle.

It is generally preferred for the handle attached to the gear to be rotatable only about 180° which, because of the variable mechanical advantage system of this invention, is sufficient to permit the first and second means to be spaced far enough apart to sufficiently space the connectors carried in the first and second means in the first position. Thus connectors can be respectively placed in the first and second means, and the handle turned to actuate the rack and gear means, causing the connectors to be driven toward each other initially rapidly, and then more slowly, with higher mechanical advantage, so that a debilitated person does not have to struggle with the final, frictional locking of the connectors into their connected relationship. Similarly, breaking of the frictional relationship between the connectors is also easy in this system.

The teeth of the rack may be positioned at differing distances from an axis of relative motion, i.e., any axis defining the relative motion between the rack and gear between the first and second positions. These differing distances of the gear teeth of the rack may correspond inversely to the differing pitches of the gear teeth, to permit relatively linear motion along the axis. Specifically, the sum of the pitch of each gear tooth and the distance from said axis of a rack tooth meshing against such gear tooth may be substantially constant from gear tooth to gear tooth along the entire length of the rack and gear system as the gear rolls along the rack. The result of this is to permit relatively linear motion of the rack along an axis between the first and second position, even though the pitches of the gear teeth are variable.

The apparatus of this invention also may include a housing, and means within the housing for providing radiation for antibacterial effect therein, specifically a source of ultraviolet irradiation.

The housing may also define drawer means carrying the first and second means for holding the connectors. This permits exposure of the connectors to the antibacterial radiation when the drawer means is closed.

The housing may also define latch means and a latch engaging site, for example an engaging hook and wall, described in greater detail below, which prevents reopening of the drawer means after initial closing until the second means is moved to the second position.

DESCRIPTION OF THE DRAWINGS

In the drawings, FIG. 1 is a fragmentary, perspective view of apparatus of this invention, shown to be holding a pair of connectors for use in peritoneal dialysis.

FIG. 2 is a fragmentary, perspective view of the apparatus of FIG. 1, showing it in an intermediate configuration of use.

FIG. 3 is a fragmentary, perspective view similar to FIG. 1, showing the apparatus of this invention after the connection between the connectors has been made and the antibacterial radiation process has been applied.

DESCRIPTION OF SPECIFIC EMBODIMENT

Figure 9:
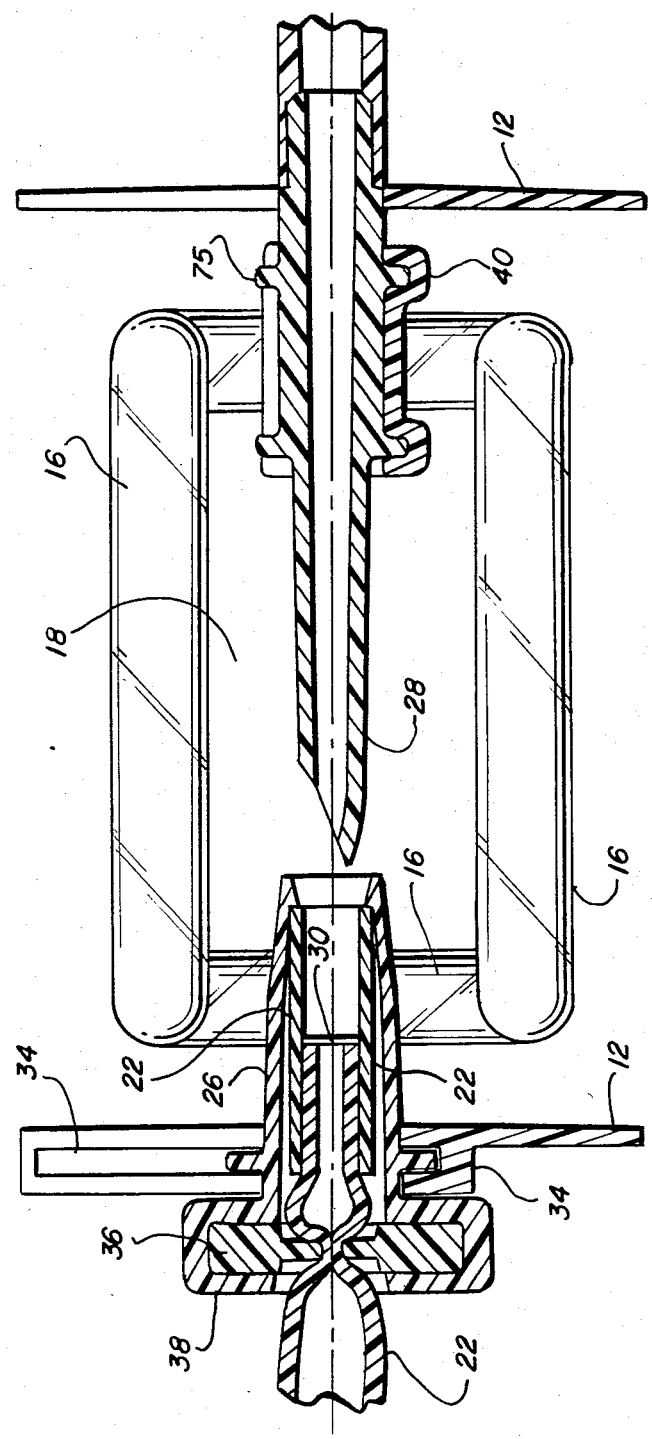
FIG. 9 is a fragmentary transverse sectional view of the apparatus of this invention taken along line 9—9 of FIG. 6.

Referring to FIGS. 1-3, the apparatus 10 of this invention includes housing 12 and a slide drawer 14. A convoluted ultraviolet bulb 16 within housing 12 may define a channel 18 (FIG. 9) between the respective convolutions of bulb 16 into which the respective connectors 20, 22 may be placed by closing of drawer 14 for ultraviolet irradiation thereof. Connector 20 may connect to peritoneal transfer set tubing 21, while connector 22 may be a flexible, diaphragm-containing tube carried by peritoneal dialysis solution bag 24.

The design of apparatus 10 including housing 12, drawer 14, and ultraviolet bulb 16 may be generally similar to the design disclosed in the cited Hogan U.S. Pat. No. 4,433,244, except for the design changes described herein. Also, the housing, drawer, and ultraviolet bulb used in this invention may be generally similar in design except as otherwise indicated herein to the germicidal chamber currently available to the public from Travenol Laboratories, Inc. for irradiating connections in CAPD with ultraviolet radiation.

Connector 22 is positioned within a separable, molded member which comprises shaping sleeve 26 proportioned to receive the flexible end of connector 22 and to shape it as shown in FIG. 3 into a desired, circular configuration, to receive the spike 28 of connector 20, puncturing diaphragm 30 in a conventional manner. The molded member containing sleeve 26 also carries hexagonal flange 32, which can fit in first means 34 for holding connector 22, which is shown to be a generally U-shaped trough, receiving flange 32 and holding the structure in position.

The molded member also includes sliding clamp member 36, positioned in a slide box 38, which may be of the general design of analogous structure shown in Lueders et al. U.S. application Ser. No. 338,712, filed Jan. 11, 1982 and entitled "CONTINUOUS AMBULATORY PERITONEAL DIALYSIS CLAMPING SYSTEM"now U.S. Pat. No. 4,473,369, to serve as a slide clamp to control flow through the flexible tubing which comprises connector 22, connected to peritoneal dialysis solution bag 24.

Second connector 20 is carried by second means 40 for holding the connector. Second means 40, as shown by FIGS. 4-7, is carried as part of a rack and gear system including rack 42 and gear 44. Rack 42 is attached to and can move with plate 43, while gear 44 is in a fixed position. Second means 40 is shown to be attached to rack 42 and to slide in a track groove 46 defined by the front panel 48 of drawer 14.

Gear 44 rotates about shaft 50, which terminates in handle 51. As handle 51 is rotated, gear 44 correspondingly rotates, to move rack 42 between the respective first and second positions illustrated respectively in FIGS. 1 and 4, and FIGS. 3 and 5. Rack and gear systems 42, 44 can be purchased from Cunningham Industries of Stamford, Conn.

It can be seen that teeth 52 of gear 44 define increasing pitch (distance) from the center of each gear tooth 52 to the center or axis of rotation 54, extending approximately 180° about gear 44, so that the pitch or distance of gear tooth 52a from center of rotation 54 is much greater than the corresponding pitch or distance of gear tooth 52b.

It can also be seen that teeth 56 of rack 42 are correspondingly not in parallel array with axis of rack movement 58 between the first and second positions, but are positioned at differing distances from axis 58 so that rack tooth 56a is closer to axis 58 than rack tooth 56b. The spacing from axis 58 of the respective teeth 56 corresponds inversely to the differing pitches of gear teeth 52 so that rack 42 can move in relatively linear motion along axis 58. Specifically, the sum of the pitch of each gear tooth 52 and the distance from axis 58 of a rack tooth 56 meshing against such gear tooth is substantially constant. In other words, the sum of the pitch 53 of gear tooth 52a from axis of rotation 54 and the perpendicular distance 55 of rack tooth 56a from axis 58 (FIG. 4) should be substantially equal to the corresponding pitch of gear tooth 52b plus the distance from axis 58 of rack tooth 56b. Thus as the pitch of each gear tooth increases, the perpendicular distance of each rack tooth from axis 58 correspondingly decreases. This permits substantially linear, perpendicular motion of rack 42 relative to axis of rotation 54.

Drawer 14 is conventionally slidable into and out of housing 12, taking first means 34 and second means 40 for holding the respective connectors with it. As shown, first means 34, the U-shaped trough, is open at the top and defined in a side wall of drawer 14. On the opposite side wall of drawer 14 an open slot 60 is provided to receive connector 20 of tubing 21 in sliding relation to it. Housing 12 carries horizontal slots to intersect the slots defined by first means 34 and slot 60, to permit closing of drawer 14 with the respective connectors in place. The specific design may be similar to the currently available Travenol germicidal chamber or the previously cited Hogan patent application.

Figures 4, 5:
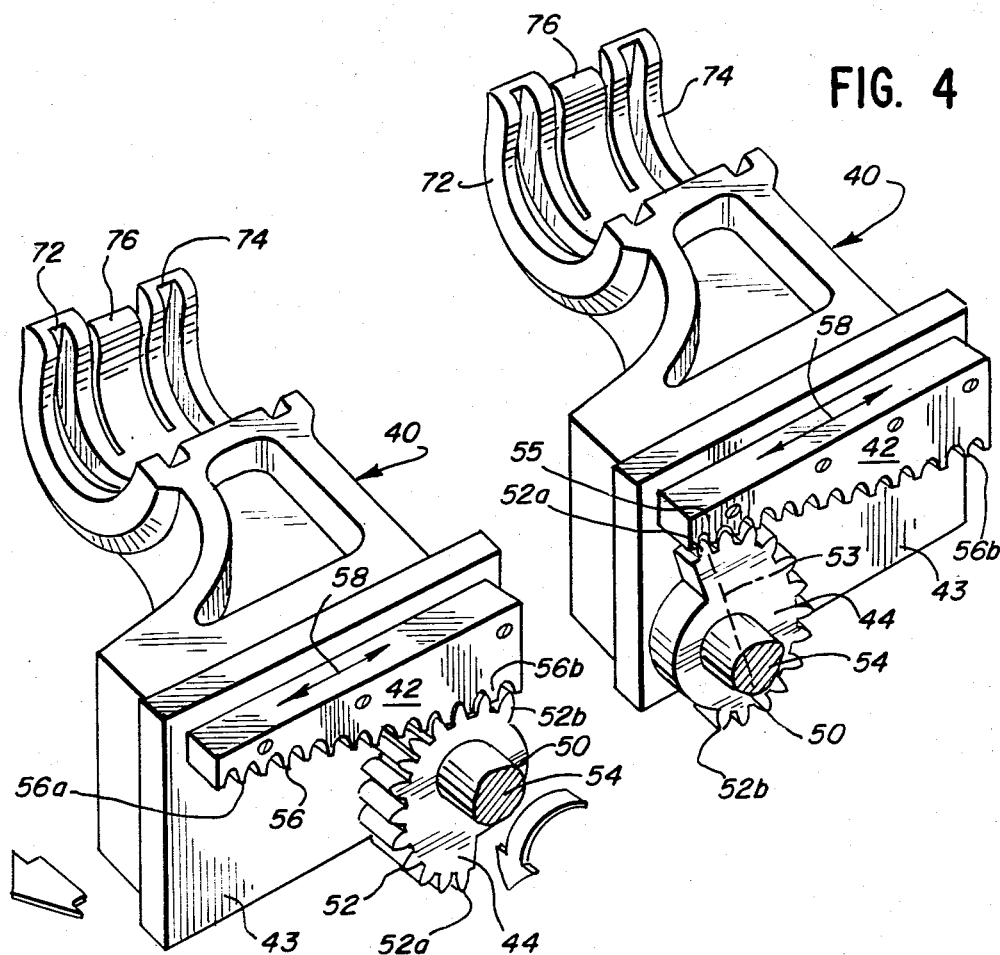
FIGS. 4 and 5 are fragmentary perspective views of the second means and the rack and gear means of this invention, shown in different positions.
Figure 6:
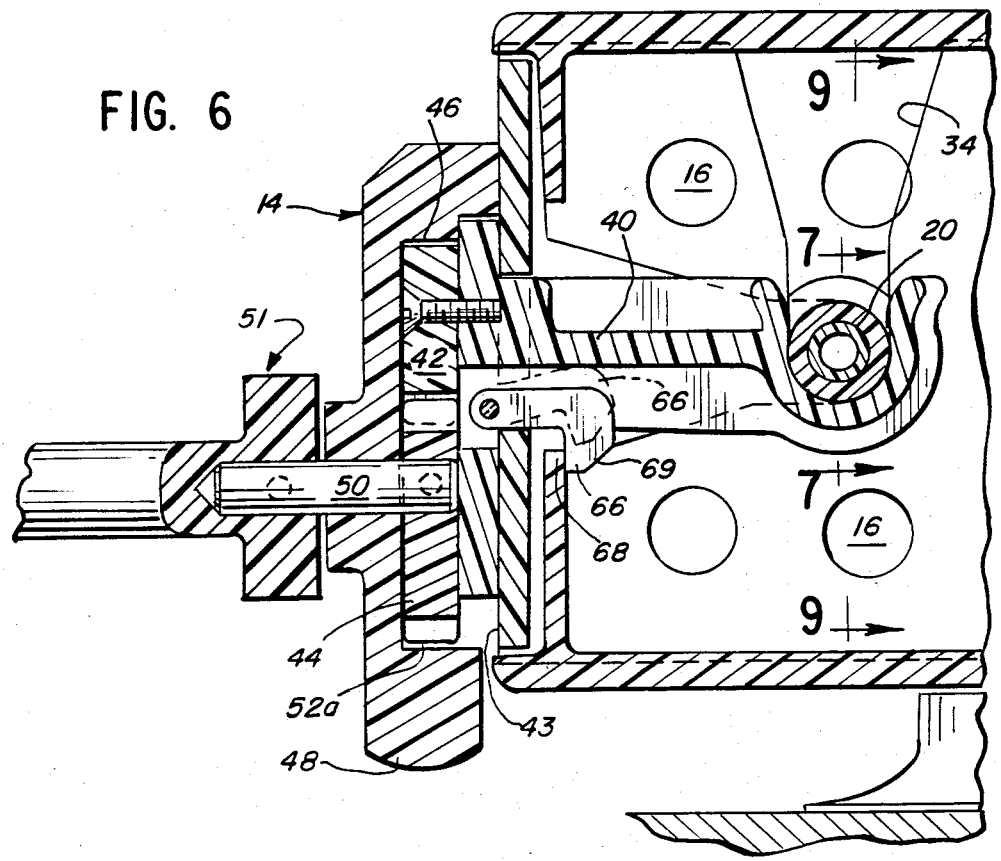
FIG. 6 is a fragmentary, longitudinal sectional view of the apparatus of this invention with the drawer closed.

Turning particularly to FIG. 6, drawer 14 is shown to carry pivotable latch hook means 66, which is positioned to latch against latch wall 68 of housing 12 as the latch engaging site (see FIGS. 1, 3, and 6) for engagement of pivotable latch hook 66 and latch wall 68 in the first position of second means 40, i.e., when the connectors are separated, and when the drawer means 14 is closed. As shown in FIG. 6, latch hook means 66 defines an angled face 69 which causes latch hook 66 to deflect upwardly as drawer 14 is closed when it impinges latch wall 68. As drawer 14 completes the closing action, latch hook 66 falls back again as shown in FIG. 6, to prevent reopening of the drawer in that position.

However, as shown in FIGS. 1 and 3, the latch wall 68 only extends across a portion of the width of housing 10, with a reduced height wall 70 occupying substantially the remainder of the width of the housing. Accordingly, as second connector holding means 40 is moved by rotation of handle 51 toward the first, connected position, latch hook 66 which is carried with it is moved out of engagement with latch wall 68, being capable of passing over the top of reduced height wall 70. Thus drawer 14 can be opened after closing, when handle 51 is rotated as shown in FIG. 2 to move second means 40 into the first, connected position.

Other designs of latch means and latch engaging site may also be used.

Figure 8:
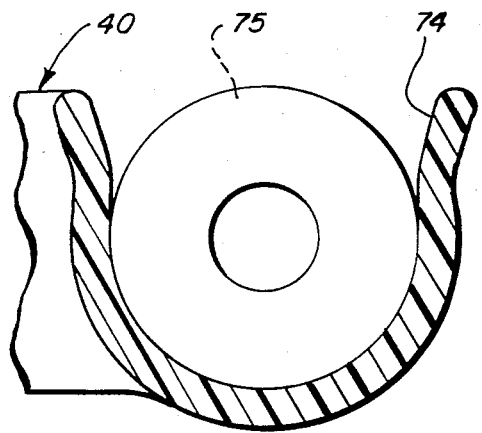
FIG. 8 is a fragmentary sectional view taken along line 8—8 of FIG. 7.
Figure 7:
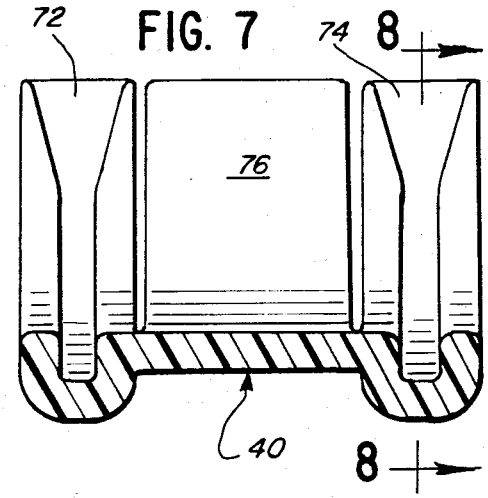
FIG. 7 is a sectional view taken along line 7—7 of FIG. 6.

Referring to FIGS. 7 and 8, it can be seen that second connector holding means 40 defines a pair of slots 72, 74 for receiving corresponding flanges 75 of a connector 20 as shown in FIGS. 1 and 3. A separate partially cylindrical portion 76 is also provided, defining spring arm means for releasably retaining connector 20. Thus, connector 20 can snap into and out of retained relationship with second means 40.

For use of the apparatus of this invention, a patient on CAPD has typically drained spent dialysis solution from his peritoneal cavity through tubing 21 and connectors 20 and 22 into a bag 24. He then inserts connectors 20 and 22 into first and second holding means 34, 40 with drawer 14 and handle 51 in the position of FIG. 3. Handle 51 is then rotated to the FIG. 1 position, separating connector 20 from connector 22. Bag 24 and connector 22 are then replaced with a fresh bag 24 and connector 22, and drawer 14 is closed to begin irradiation. Line 21 may be closed off with a slide clamp or the like in conventional manner. The molded structure comprising sleeve 26 is placed onto port 22 of the fresh bag of dialysis solution 24 to seat it in the first connector holding means 34 with slide clamp 36 being closed.

Ultraviolet lamp system 16 is activated by the closing of the drawer in a manner which may be similar to the electronic system of the Travenol germicidal chamber, with the ultraviolet irradiation continuing until the desired level of irradation is achieved. This can be signaled to the patient by known circuitry, and an indicator light or buzzer, following which the patient rotates handle 51 again to the configuration shown in FIG. 2, causing the respective connectors to connect into flow relationship with each other. Thereafter, the patient opens drawer 14 again as in FIG. 3, and removes the newly connected system. He then opens clamp 36 and the clamp on tubing 21 to cause the fresh peritoneal dialysis solution to flow from bag 24 through tubing 21 into the patient's peritoneal cavity.

As the result of this, even a debilitated patient can make connections with ease, and with improved reliability of aseptic conditions, with the ultraviolet light irradiation greatly reducing the risk of contamination and consequent peritonitis. The respective parts exposed to ultraviolet light such as spike 20 and sleeve 26, may be made of known ultraviolet transparent materials so that their interiors as well as their exteriors may be irradiated for antibacterial effect.

The above has been offered for illustrative purposes only, and is not intended to limit the scope of the invention of this application, which is as defined in the claims below.

That which is claimed is:

1. In apparatus for automatically connecting and disconnecting a pair of connectors, including a housing; means within said housing for providing radiation for antibacterial effect therein; first and second means for respectively holding said connectors, said first and second means being relatively movable between first and second positions, to cause connectors carried in the first and second means to be separated from each other in the first position, and to cause said carried connectors to be joined together in the second position; rack and gear means for relatively moving said first and second means between said first and second positions, the gear of said rack and gear means defining gear teeth of increasing pitch from its center of rotation about at least a portion of its periphery, the rack of said rack and gear means defining mating teeth correspondingly spaced along its length in positions to permit relatively linear motion between said rack and gear as the gear rolls along the rack, whereby the mechanical advantage of the rack and gear means varies with the position of the gear along the rack.

2. The apparatus of claim 1 in which said mechanical advantage is substantially at its maximum when the rack and gear means are at the second position.

3. The apparatus of claim 1 in which the teeth of said rack are positioned at differing distances from an axis of relative motion of the first and second means between the first and second positions, said differing distances inversely corresponding to the differing pitches of the gear teeth to permit relatively linear motion along said axis.

4. The apparatus of claim 3 in which the sum of the pitch of each gear tooth and the distance from said axis of a rack tooth meshing against said gear tooth is substantially constant from gear tooth to gear tooth.

5. The apparatus of claim 1 in which said radiation providing means is a source of ultraviolet radiation.

6. The apparatus of claim 1 in which said housing defines drawer means, said drawer means carrying said first and second means to permit exposure of said connector to antibacterial radiation when the drawer means is closed.

7. The apparatus of claim 1 in which one of said housing and second means defines latch means, said second means being movable by the rack and gear means, and the other of said housing and second means defining a latch engaging site positioned to engage said latch means in the first position and to be spaced from the latch means in the second position, whereby said drawer means cannot be reopened after closing until said second means is moved to the second position.

8. The apparatus of claim 1 in which one of said first and second means defines spring arm means for releasably retaining a connector.

9. The apparatus of claim 1 in which said second means for holding the connectors is movable by said rack and gear means between the first and second positions, said gear of the gear means being attached to a rotatable shaft, whereby rotation of such shaft and gear causes said rack to move in a direction transverse of said shaft, said shaft terminating in a rotatable handle.

10. The apparatus of claim 9 in which said shaft carries rotatable handle means adapted to rotate substantially 180° to cause said second means to move between the first and second positions.

11. An apparatus for automatically connecting and disconnecting a pair of connectors, including a housing, and means within said housing for providing radiation for antibacterial effect therein; first and second means for respectively holding said connectors, said second means being relatively movable between first and second positions to cause connectors carried in the first and second means to be separated from each other in the first position and to cause said carried connectors to be joined together in the second position, rack and gear means for relatively moving said first and second means between said first and second positions, the gear of said rack and gear means defining gear teeth of increasing pitch from its center of rotation about at least a portion of its periphery, the rack of said rack and gear means defining teeth which are positioned at differing distances from an axis of relative motion of the first and second means between the first and second positions, said differing distances inversely corresponding to the differing pitches of the gear teeth to permit relatively linear motion along said axis between said rack and gear as the gear rolls along the rack, whereby the mechanical advantage of the rack and gear means varies with the position of the gear along the rack, said mechanical advantage being substantially at its maximum when the rack and gear means are at the second position.

12. The apparatus of claim 11 in which the sum of the pitch of each gear tooth and the distance from said axis of a rack tooth meshing against said gear tooth is substantially constant from gear tooth to gear tooth.

13. The apparatus of claim 12 in which said radiation providing means is a source of ultraviolet radiation.

14. An apparatus for automatically connecting and disconnecting a pair of connectors, including first and second means for respectively holding said connectors, said first and second means being relatively movable between first and second positions to cause connectors carried in the first and second means to be separated from each other in the first position, and to cause said carried connectors to be joined together in the second position, rack and gear means for relatively moving said first and second means between said first and second positions, the gear of said rack and gear means defining gear teeth of increasing pitch from its center of rotation about at least a portion of its periphery, the rack of said rack and gear means defining mating teeth correspondingly spaced along its length in positions to permit relatively linear motion between said rack and gear as the gear rolls along the rack, whereby the mechanical advantage of the rack and gear means varies with the position of the gear along the rack, said apparatus including a housing, and means within said housing for providing radiation for antibacterial effect therein, said housing defining drawer means, said drawer means carrying said first and second means to permit exposure of said connectors to antibacterial radiation when the drawer means is closed, one of said drawer means and second means defining latch means, said second means being movable by the rack and gear means, and the other of said drawer means and second means defining a latch engaging site positioned to engage said latch means in the first position and to be spaced from the latch means in the second position, whereby said drawer means cannot be reopened after closing until said second means is moved to the second position.

15. The apparatus of claim 14 in which the mechanical advantage of the rack and gear means is substantially at its maximum when the rack and gear means are at the second position, the teeth of said rack being positioned at differing distances from an axis of relative motion of the first and second means between the first and second positions, said differing distances inversely corresponding to the differing pitches of the gear teeth to permit relatively linear motion along said axis.

16. The apparatus of claim 15 in which one of said first and second means defines spring arm means for releasably retaining a connector.

17. The apparatus of claim 18 in which said second means for holding the connectors is movable by said rack and gear means between the first and second positions, said gear of the gear means being attached to a rotatable shaft whereby rotation of such shaft and gear causes said rack to move in a direction transverse of said shaft, said shaft terminating in a rotatable handle.

18. The apparatus of claim 17 in which said shaft carries rotatable handle means adapted to rotate substantially 180° to cause said second means to move between the first and second positions.

19. An apparatus for automatically connecting and disconnecting a pair of connectors, including a housing; means within said housing for providing radiation for antibacterial effect therein; first and second means for respectively holding said connectors, said first and second means being relatively movable between first and second positions, to cause connectors carried in the first and second means to be separated from each other in the first position, and to cause said carried connectors to be joined together in the second position; means for moving said second means between said first and second positions; said housing carrying said first and second means, to permit exposure of said connector to antibacterial radiation when the drawer is closed and to provide access to said connector when the drawer is open, one of said housing and second means defining latch means, the other of said housing and second means defining a latch engaging site positioned to engage said latch means in the first position and to be spaced from the latch means in the second position, whereby said housing cannot be reopened after closing until said second means is moved to the second position.

20. The apparatus of claim 19 in which said radiation providing means is a source of ultraviolet radiation.

21. The apparatus of claim 19 in which said second means for holding the connectors is movable by rack and gear means between the first and second positions, said gear of the gear means being attached to a rotatable shaft, whereby rotation of said shaft and gear causes said rack to move in a direction transverse of said shaft, said shaft terminating in a rotatable handle.

22. The apparatus of claim 21 in which said shaft and rotatable handle is adapted to rotate substantially 180° to cause said second means to move between the first and second position.

* * * * *